United States Patent [19]
Grund

[11] Patent Number: 5,420,361
[45] Date of Patent: May 30, 1995

[54] FORMULATION OF AND DEHYDRATION OF HYDROXYLATED DIPHENYL ACETYLENES

[75] Inventor: Alan D. Grund, Manitowoc, Wis.

[73] Assignee: Bio-Technical Resources, Manitowoc, Wis.

[21] Appl. No.: 240,125

[22] Filed: May 10, 1994

Related U.S. Application Data

[62] Division of Ser. No. 831,585, Feb. 5, 1992, abandoned.

[51] Int. Cl.⁶ ............... C07C 37/00; C07C 39/21
[52] U.S. Cl. ................ 568/717; 568/716; 568/731; 568/743; 568/744; 568/745
[58] Field of Search ............... 568/720, 717, 731, 743, 568/744

[56] References Cited

U.S. PATENT DOCUMENTS

| | | | |
|---|---|---|---|
| 4,081,468 | 3/1978 | Baker et al. | 260/551 R |
| 4,153,509 | 5/1979 | Schwartz | 195/51 R |
| 4,508,822 | 4/1985 | Taylor | 435/155 |
| 4,532,209 | 7/1985 | Hogedom | 435/156 |
| 4,603,187 | 7/1986 | Choe | 526/285 |
| 4,772,755 | 9/1988 | Liotta et al. | 568/646 |
| 4,876,200 | 10/1989 | Schofield et al. | 435/253.5 |
| 4,954,659 | 9/1990 | Parkhurst et al. | 568/717 |
| 4,956,502 | 9/1990 | Wenteler et al. | 568/717 |
| 4,978,810 | 12/1990 | Kanayama et al. | 568/720 |
| 4,981,793 | 1/1991 | Johnson et al. | 435/128 |
| 5,036,009 | 7/1991 | Taylor | 435/2533 |

*Primary Examiner*—Werren B. Lone

[57] ABSTRACT

The production of cis-dihydrodiol compounds of the formula

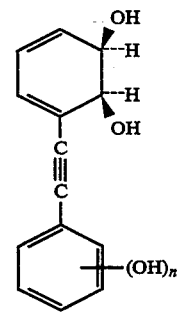

where n is 0 or 1 (preferably 0) by the microbial oxidation of a diphenylaceylene compound of the formula

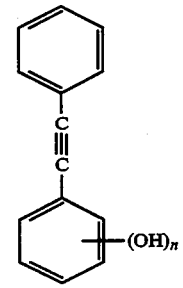

using a mutant of a Pseudomonas bacteria at 25° to 35° C. and pH 6-8 is disclosed. The cis-dihydrodiol compound is in turn treated with an aqueous solution of a base to produce a corresponding 3-hydroxydiphenylacetylene compound or with an aqueous solution of an acid to produce a corresponding 2-hydroxyacetylene compound.

7 Claims, No Drawings

FORMULATION OF AND DEHYDRATION OF HYDROXYLATED DIPHENYL ACETYLENES

CROSS-REFERENCE TO RELATED APPLICATIONS

This application is a divisional application of copending U.S. application Ser. No. 07/831,585, filed Feb. 5, 1992, abandoned for "Formation Of And Dehydration Of Hydroxylated diphenyl Acetylenes."

BACKGROUND OF THE INVENTION

1. Field of the Invention

The present invention relates to the production of the cis-dihydrodiol derivative of diphenylacetylenes and the dehydration thereof to form the corresponding meta-substituted phenol derivative. Use of alkali, preferably at elevated temperature, optimizes production of 3-hydroxydiphenylacetylene over 2-hydroxydiphenylacetylene.

2. Description of the Related Art

Compounds of the general formula

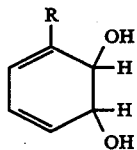

have been chemically dehydrated to phenols by acidification. In general, the 2-hydroxy isomer predominates, or is the exclusive product of the reaction. More recently, U.S. patent application Ser. No. 07/623,581, filed Dec. 7, 1990, discloses the use of a base to optimize production of the 3-hydroxy isomer of certain such compounds.

U.S. Pat. No. 4,508,822 discloses the preparation of compounds of the general formula

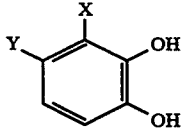

wherein X and Y may be the same or different, and represent hydrogen, halogen, or cyano groups except that X and Y cannot both be hydrogen, using strains of *Pseudomonas putida*.

U.S. Pat. No. 4,532,209 discloses the production of p-cresol by the acidification of an aqueous solution of 4-methylcyclohexa-3,5-diene-1,2-diol-1-carboxylic acid.

The formation of (+)-cis-2,3-dihydroxy-1-methylcyclohexa-4,6-diene from toluene by Pseudomonas putia, is disclosed by D. T. Gibson et al., Biochemistry, pp. 1626–1630, Vol. 9, (1970) along with the acid catalyzed dehydration of ( +)-cis-2,3-dihydroxy-1-methylcyclohexa -4,6-diene.

U.K. Patent No. 2,203,150 B discloses preparing fluorophenols by dehydrating 1,2-dihydroxy-3-fluorocyclohexa-3,5-diene in the presence of base and subsequently recovering 2 and/or 3-fluorophenol. The use of base does not make the reaction overly selective for 3-fluorophenol.

Initial Reactions in the Oxidation of Ethylbenzene by Pseudomonas putida, by D. T. Gibson et al., Biochemistry, pp. 1520–1527, Vol. 12, No. 8, (1973) discloses the oxidation of ethyl benzene to (+)-cis-3-ethyl-3,5-cyclohexadiene-1,2-diol and (+)-cis-3-(1'-hydroxyethyl)-3,5-cyclohexadiene-1,2-diol by Pseudomonas putida as well as the oxidation of acetophenone to cis-3-(1'-oxoethyl)-3,5-cyclohexadiene-1,2-diol. The reference also discloses the acid catalyzed dehydration of (+)-cis-3-ethyl-3,5-cyclohexadiene-1,2-diol.

Biodegradations Yield Novel Intermediates For Chemical Synthesis, D. W. Ribbons et al., Biotechnology and Biodegradations, pp. 213–245, London discloses the use of mutants of P. putida to form compounds of the formula

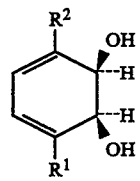

where $R^1=R^2=H$; $R^1=Cl$, $R^2=H$; $R^1=F$, $R^2=H$; $R^1=CH_3$, $R^2=H$; $R^1=Ph$, $R^2=H$; $R^1=CF_3$, $R^2=H$; $R^1=C_2H_5$, $R^2=H$; $R^1=HC=CH_2$, $R^2=H$; $R^1=C=CH$, $R^2=H$; $R^1=CH^3R^2=F$; $R^1=CH^3R^2=Cl$; $R^1=CH_3$, $R^2=Br$.

U.S. Pat. No. 4,081,468 discloses acetylenic compounds of the formula $R^3-C=C-R^4$ where $R^3$ is selected from the group consisting of hydroxy, hydroxyalkyl, hydroxyalkenyl, hydroxyalkynyl, hydroxy substituted cycloalkyl, hydroxy substituted phenyl, hydroxy substituted phenalkyl, amino substituted alkyl and alkyl substituted by the group -O-C(O)-alkyl, and $R^4$ is selected from the group consisting of hydrogen, alkyl, alkenyl, alkynyl, cycloalkyl, phenyl, phenalkyl, hydroxyalkyl, hydroxyalkenyl, hydroxy cycloalkyl, hydroxyalkenyl, hydroxy cycloalkyl, hydroxy substituted phenyl, hydroxy substituted phenalkyl, amino alkyl and alkyl substituted by the group -O-C(O)-alkyl.

U.S. Pat. No. 4,153,509 discloses preparing compounds of the formula

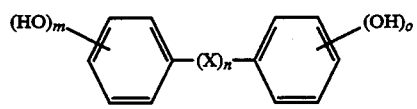

wherein, m and o are individually 1 or 0 with the proviso that both m and o may not be 0, n is 0, 1 or 2; and x is phenyl, divalent oxygen, sulfur, sulfinyl, sulfonyl, carbonyl, amino or alkylamino or x is a divalent alkylene, alkenylene or alkynylene chain which may optionally include one or more divalent oxygen, sulfur, sulfinyl, sulfonyl, carbonyl, amino or alkylamino moieties in any combination by enzymatically biotransforming the corresponding biphenyl compound with a microorganism.

U.S. Pat. No. 4,772,755 discloses compounds of the formula

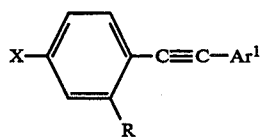

wherein x is hydroxy, alkoxy or alkanoyloxy, Ar[1] is an organic group such as phenyl which may be independently substituted by one or more of alkyl, alkoxy, alkylthio, dialkylamino, halogen etc. and R is an unsubstituted or substituted alkyl group.

EP 400,779 A1 discloses production of meta-hydroxypheny-acetylenes from phenyl-substituted ketal or acetal precursors.

SUMMARY OF THE INVENTION

The present invention relates to the preparation of 3-hydroxydiphenylacetylene or less preferably 2-hydroxydiphenylacetylene. The first step in the process is the preparation of diphenylacetylene-cis-2, 3-dihydrodiol by the microbial oxidation of diphenyl acetylene. The diphenylacetylene-cis-2,3-dihydrodiol is then dehydrated with a base at an elevated temperature to produce 3-hydroxydiphenylacetylene. Alternatively, the diphenylacetylene-cis-2,3-dihydrodiol can be dehydrated with an acid to produce 2-hydroxydiphenylacetylene.

DESCRIPTION OF THE PREFERRED EMBODIMENTS

The first aspect of the present involves the production of diphenylacetylene-cis-2,3-dihydrodiol from diphenylacetylene. This is done by microbial oxidation using a suitable bacteria. Generally, a bacterium is isolated by enrichment technique from the environment or obtained from a depository. The first criterium for the bacterium is that it is capable of growth on biphenyl as the sole carbon and energy source. Generally, suitable bacteria are of the genus Pseudomonos and, more specifically, are mutants of Pseudomonas Strain 73. Strain 73 is a mobile, anaerobic bacterium having a rod morphology (1×3 microns). It is gram negative strain reaction, is catalase and oxidase positive, and utilizes glucose strictly in an oxidative manner. The organism is negative for the production of pigments, accumulation of poly-$\beta$-hydroxybutyrate (PHB), hydrolysis of gelatin, or formation of nitrogen from nitrate. The organism has no requirement for specific growth factors and does not grow at 41° C. The starting strain is then treated with N-methyl-N'-nitro-N-nitrosoquanidine or ultraviolet light in the known manner to effect mutagenesis to obtain mutants which are unable to grow on biphenyl. Certain of these mutants will be found which lack a functional dihydrodiol dehydrogenase. When such mutants are grown on a defined minimal salts medium containing a carbon source such as glucose or succinate and exposed to diphenyl acetylene, a colorless metabolite accumulates in the growth medium with an ultraviolet light (UV) absorbance maximum at 321 nm. This UV absorbing metabolite is the cis-2,3-dihydrodiol of diphenylacetylene, and can accumulate in the growth medium at concentrations of from 100 parts per million (ppm) to 1,000 ppm or even higher, depending on growth conditions. This dihydrodiol can then be dehydrated either to the 2- or 3-hydroxydiphenylacetylene phenol as described below. ATCC strain number 55272 is a Pseudomonas Strain 73-4, a mutant of Pseudomonas Strain 73, described above. This mutant possesses all of the characteristics of a Pseudomonas Strain 73, with the exception that the bacterium is incapable of growth on biphenyl and that it lacks the diol dehydrogenase activity which converts aromatic cis-dihydrodiols to catechols. The strain was received by the American Type Culture Collection, 12301 Parklawn Drive, Rockville, Md. on Jan. 6, 1992 and was designated ATCC number 55272.

Generally, a cell-free aqueous broth containing the cis-2,3-diol of diphenylacetylene at a concentration of 100 to 5,000 ppm is used. To optimize dehydration to the meta-phenol (3-hydroxydiphenylacetylene) the broth is quickly heated to 50° to 120° C, preferably from 75° to 100° C. Then a solution of base at the elevated temperature is quickly added and mixed. The final concentration of base is at least 0.1N, preferably 1.0N or higher up to 8.0N. The solution is held at the elevated temperature for at least 15 minutes, preferably for longer times of 1 to 10 hours. The mixture is then cooled to 20° to 30° C. and the phenols recovered such as by extraction with organic solvents. The preferred bases are sodium hydroxide, potassium hydroxide and cesium hydroxide, with sodium hydroxide preferred because of cost. The conversion to the 3-hydroxydiphenylacetylene isomer is 100% when the process is operated under optimum conditions.

The compounds produced by the present invention are useful as intermediates for producing polymeric materials.

Generally the reactions of the present invention can be represented by the following reaction schemes I, II or III.

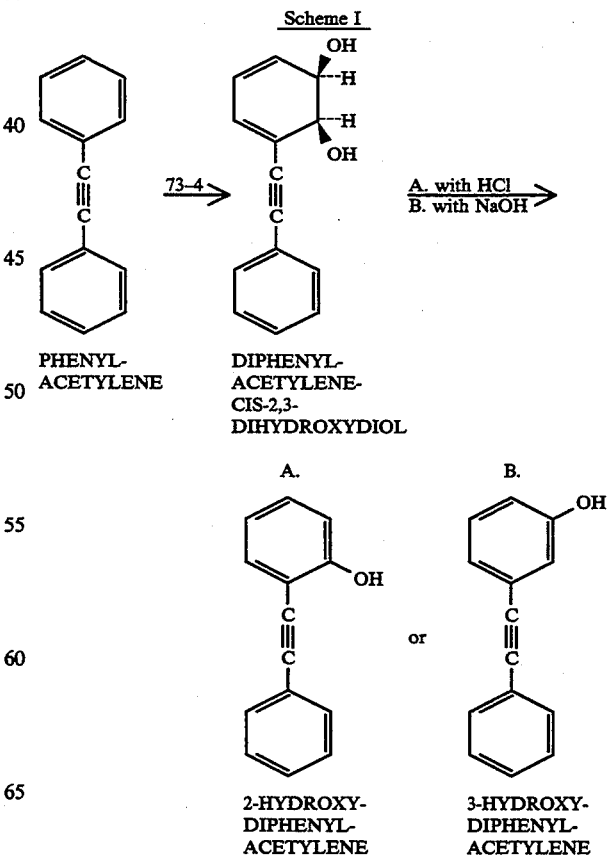

SCHEME II

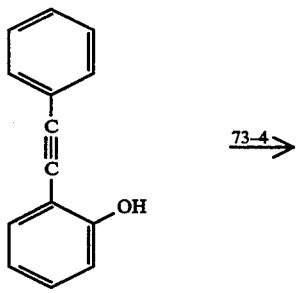

2-HYDROXYDIPHENYL
ACETYLENE

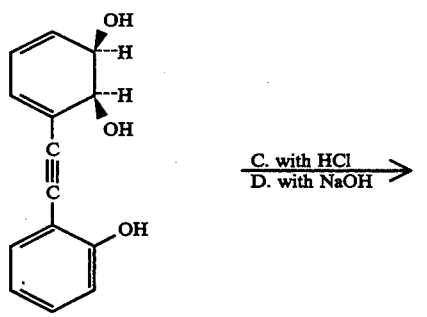

2'-HYDROXYDIPHENYL-
ACETYLENE-CIS-2,3-
DIHYDROXYDIOL

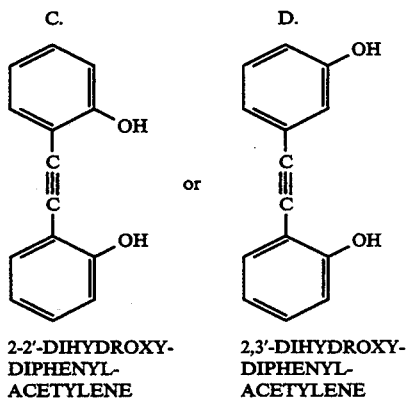

2-2'-DIHYDROXY-
DIPHENYL-
ACETYLENE 2,3'-DIHYDROXY-
DIPHENYL-
ACETYLENE

SCHEME III

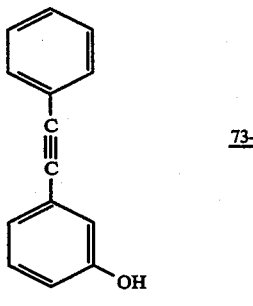

3-HYDROXYDIPHENYL
ACETYLENE

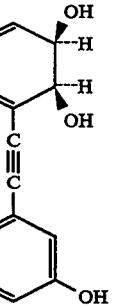

-continued
SCHEME III

3'-HYDROXYDIPHENYL-
ACETYLENE-CIS-2,3-
DIHYDROXYDIOL

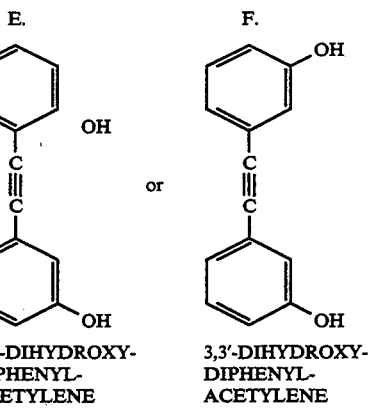

2-3'-DIHYDROXY-
DIPHENYL-
ACETYLENE 3,3'-DIHYDROXY-
DIPHENYL-
ACETYLENE

The composition of the minimal salts (MS) medium used in the following Example 1 in grams per liter was as follows: NH$_4$Cl, 1.0; NaNO$_3$, 1.0; MgSO$_4$, 0.16; FeSO$_4 \sim$7H$_2$O, 0.004; K$_2$HPO$_4$, 4.4; KH$_2$PO$_4$, 3.4; trace salts (TS) solution, 2 ml; and distilled water, 1 liter. The pH of the medium was adjusted to 7.0 using HCl as required. The trace salts solution consisted in grams per liter: concentrated HCl, 10 ml; CuSO$_4 \sim$5H$_2$O, 0.063; CoCl$_2 \sim$6H$_2$O, 0.16; H$_3$BO$_3$, 0.91; ZnSO$_4 \sim$7H$_2$O, 1.8; MnSO$_4 \sim$H$_2$O, 1.2; NaMoO$_4 \sim$2H$_2$O, 0.048; CaCl$_2 \sim$2-H$_2$O, 11.4, VSO$_4 \sim$2H$_2$O, 0.08, Ni(NO$_3$)$_2 \sim$6H$_2$O, 0.04; Na$_2$SeO$_3$, 0.04; and distilled water, 980 ml. Carbon sources were added from sterile stock solutions to autoclaved media (1% final concentration).

EXAMPLE 1

Pseudomonas strain 73-4, ATCC 55272, a mutant of Pseudomonas strain 73, lacking a functional diol dehydrogenase, was grown in the MS medium described above plus 1% succinic acid as carbon source. The organism was grown in 100 ml of medium in a 500 ml shake flask agitated at 150 RPM at 30° C. Diphenylacetylene was provided as solid crystals added to the growth medium. After 16 hours incubation the cells were removed by centrifugation and the broth assayed for the diol of diphenylacetylene by gas chromatography. The compound was present at 320 ppm.

EXAMPLE 2

Pseudomonas strain 73-4 was grown in the MS medium as described in Example 1, but with glucose as the sole carbon and energy source. Exposure to diphenylacetylene for 16 hours resulted in formation of diphenylacetylene-cis-2,3-dihydrodiol at a concentration of 125 ppm.

EXAMPLE 3

Diphenylacetylene-cis-2,3-dihydrodiol was produced to a concentration of 150 ppm using a microorganism isolated from the environment and a process similar to that described in Example 1. Following removal of the cells by centrifugation, the crude broth containing the dihydrodiol was divided into four portions and treated as described in the Table below.

TABLE

| Treatment of Diphenylacetylene-cis-2,3,-dihydrodiol | Products of Dehydration | |
|---|---|---|
| | 2-hydroxy-diphenylacetylene % | 3-hydroxy-diphenylacetylene % |
| 1.0N HCl/25° C./1 hour | 93 | 7 |
| 1.0N HCl/75° C./1 hour | 65 | 35 |
| 1.0N NaOH/25° C./1 hour | 86 | 14 |
| 1.0N NaOH/75° C./1 hour | 0 | 100 |

Having thus described and exemplified the invention with a certain degree of particularity, it should be appreciated that the following claims are not to be so limited but are to be afforded a scope commensurate with the wording of each element of the claim and equivalents thereof.

I claim:

1. A process comprising treating an aqueous solution of a starting compound of the formula

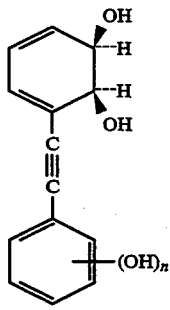

where n is 0 or 1, at a temperature of 50° to 120° C. with an aqueous basic solution at about the same temperature to bring the normality of the resulting basic solution to at least 0.1 and maintaining about the same for at least 15 minutes and producing a compound of the formula

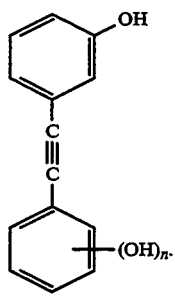

2. The process of claim 1 wherein the starting compound has the formula

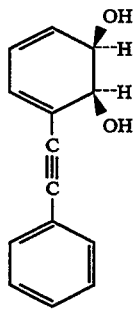

and the product compound has the formula

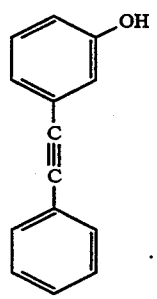

3. The process of claim 2 wherein the resulting solution contains at least about 1.0 N base.

4. The process of claim 3 wherein the base is sodium hydroxide, potassium hydroxide or cesium hydroxide.

5. The process of claim 4 wherein the temperature if from about 75° to 100° C.

6. The process of claim 5 wherein the basic solution is held at 75° to 100° C. for about 1 to about 10 hours.

7. The process of claim 5 wherein from 100 to 5,000 ppm of the starting compound is present.

* * * * *